United States Patent [19]

Hachmann

[11] Plant 4,905

[45] Oct. 26, 1982

[54] RHODODENDRON PLANT—HACPUT VARIETY

[75] Inventor: Johannes Hachmann, Barmstedt in Holstein, Fed. Rep. of Germany

[73] Assignee: Conard-Pyle Company, West Grove, Pa.

[21] Appl. No.: 162,916

[22] Filed: Jun. 25, 1980

[51] Int. Cl.[3] ..... A01H 5/00

[52] U.S. Cl. ..... Plt./55

[58] Field of Search ..... Plt./55

*Primary Examiner*—James R. Feyrer

*Attorney, Agent, or Firm*—Burns, Doane, Swecker & Mathis

[57] ABSTRACT

A new and distinct variety of *Rhododendron russatum* which originated as a chance seedling in a cultivated area is provided. The new variety possesses flowers which are of a highly attractive violet-blue color, and exhibits good tolerance to extremes in temperature.

2 Drawing Figures

SUMMARY OF THE INVENTION

The new variety was discovered and selected by me as a chance seedling of *Rhododendron russatum* while being grown among many other plants under my direction in a cultivated area at my nursery at Barmstedt in Holstein, West Germany. The seed which produced the new variety had been collected from *Rhododendron russatum* seed parents. The pollen parent was unknown since open pollination was employed.

It was an object of the selection process which resulted in the present variety to provide a new variety of blue flowered Rhododendron which would have a superior combination of characteristics when compared to other previously known generally blue flowered cultivars, such as cultivars of the *russatum* and *impeditum* species, and such well known hybrids as Blue Tit and Blue Diamond. This object was successfully achieved, and the new variety exhibits a combination of characteristics which distinguish it from all other generally blue flowered Rhododendron cultivars of which I am aware.

The following combination of characteristics is exhibited by the new variety:

(a) a bushy, well-branched and vigorous growth habit, (b) flowers of a striking violet-blue color, (c) improved hardiness compared to the *russatum* species, and (d) improved tolerance to extremes of both cold and heat when compared to the Blue Tit and Blue Diamond varieties, and varieties of the *impeditum* species.

The *russatum* species previously available generally is listed as hardy to 0°F., whereas the present variety has successfully survived temperatures of near −15° F. in a windy location at West Grove, Pa. with little or no visible damage. Similar hardiness has been observed while grown at Barmstedt in Holstein, West Germany. Additionally, the present variety has been found to thrive while grown in a humid atmosphere at West Grove, Pa. at temperatures in excess of 95° F.

Asexual reproduction of my new variety by cuttings has been accomplished at Barmstedt, West Germany, and West Grove, Pa., and demonstrates that the unique combination of characteristics has been established and is transmitted to successive generations.

The new variety has been named the Hacput variety.

BRIEF DESCRIPTION OF THE PHOTOGRAPHS

The accompanying photographs show typical specimens of my new variety of *Rhododendron russatum* as depicted in color as true as is reasonably possible to make the same in color illustrations of this character. The plants illustrated were grown at West Grove, Pa.

DETAILED DESCRIPTION

Figure 1:
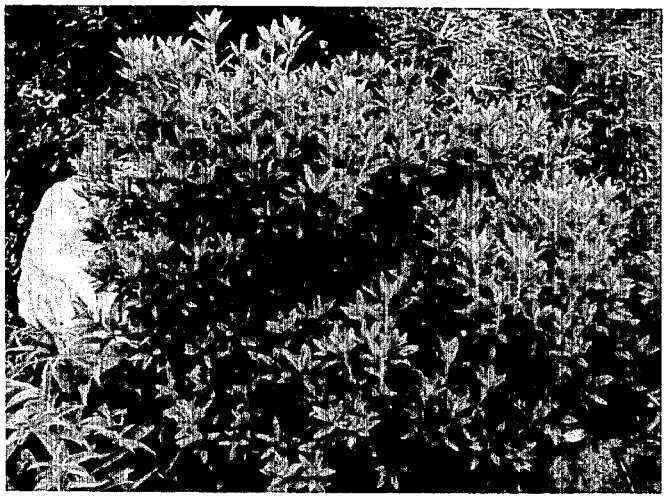
FIG. 1 illustrates the branching habit of a four year old plant being grown in the landscape during July, 1981 which is approximately 30 inches in height and approximately 40 inches in breadth. The first two years of the life of this plant were spent in a container while employing a soilless medium.
Figure 2:
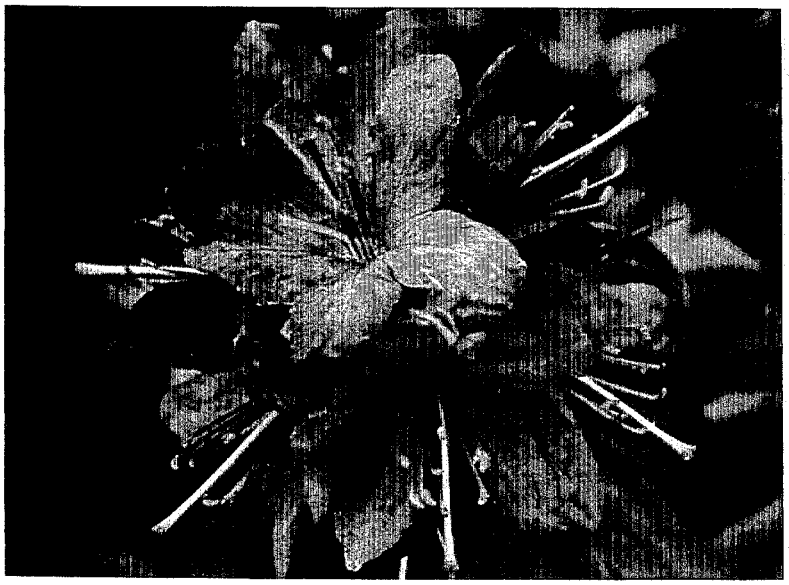
FIG. 2 illustrates the blossom and to some extent the foliage of a three year old plant. As indicated in the color chart information which follows, the color of the flower actually is less blue and more violet than indicated in the color photograph.

The following is a detailed description of my new variety with color terminology in accordance with the R. H. S. Colour Chart of the Royal Horticultural Society, London, England. The description was prepared following the observation of representative plants grown at West Grove, Pa.

Foliage:

*Type.*—Evergreen, leaves lanceolate, apex acute, base cuneate, and margins entire.

*Size.*—Length of mature leaves growing midway up stem — from approximately 4.1 to 5.2 cm. with an average of approximately 4.8 cm., and width of mature leaves growing midway up stem — from approximately 1.5 to 1.9 cm. with an average of approximately 1.7 cm.

*Color.*—Generally the color of the leaves, especially of the underside of the leaves, is influenced by the presence of rust colored scales, which is a characteristic of cultivars of the lepidote group of Rhododendron. Mature leaves observed in May, upper surface — Yellow-Green Group 147A. Under surface — closest to Yellow-Green Group 146B. Immature leaves observed in May, upper surface — Green Group 143A to 143C. Under surface — Yellow-Green Group between 144B and 145A.

Branches:

*Color.*—Very mature wood (at least two years old) — Greyed Orange Group 164A to 165B. Mature wood (one year old) — Yellow-Green Group 144B, with rust colored scales.

Flower:

*Shape and size.*—Star shaped, with five petals. Average petal length — approximately 2.5 cm. Flower diameter, fully open — from approximately 3.1 to 4.0 cm. Fully formed flower truss commonly contains five flowers. Floral buds open at West Grove, Pa. from late April to mid-May. Accordingly, the new variety commonly flowers intermediate the small leafed Rhododendron varieties such as Purple Gem, and the large leafed Rhododendron varieties such as Nova Zembla. For instance, when grown at West Grove, Pa., the buds of the Purple Gem variety commonly open during mid-April, and of the Nova Zembla variety during mid to late May. It will of course be recognized that the duration of the blooming period for the new variety will be shortened by adverse weather conditions, such as extreme heat or prolonged rain. During ideal weather conditions the blooms will commonly be exhibited upon the plants of the new variety for approximately three weeks with a given bloom having a life of approximately 5 to 7 days without any significant evidence of aging. At West Grove, Pa., the new variety commonly exhibits its maximum number of blooms at the end of April.

*Flower color.*—Open bloom — Violet Group 83D.

*Reproductive organs and floral parts.*—Stamens — ten stamens per flower. Stamen (filament) color — Violet Group 83C to 83D. Stamen length (from flower base to and including anther) — approximately 1.8 to 2.5 cm. Pistil length — from approximately 2.6 to 3.0 cm. Pedicel length — approximately 0.9 cm. on the average.

Growth habit: Bushy and well branched. Container grown plants in a soilless medium at West Grove, Pa., two years following propagation commonly average approximately 15 inches in height and approximately 15 to 18 inches in breadth.

I claim:

1. A new and distinct variety of *Rhododendron russatum,* substantially as herein shown and described, characterized particularly as to novelty by the unique combination of:

(a) a bushy, well-branched and vigorous growth habit, (b) flowers of striking violet-blue color, (c) improved hardiness compared to the *russatum* species, and (d) improved tolerance to extremes of both cold and heat when compared to the Blue Tit and Blue Diamond varieties and varieties of the *impeditum* species.

* * * * *